United States Patent
Lust

(10) Patent No.: US 11,840,464 B2
(45) Date of Patent: *Dec. 12, 2023

(54) SYSTEMS AND METHODS FOR OZONE WATER GENERATOR

(71) Applicant: Northstar Medical Technologies, LLC, Beloit, WI (US)

(72) Inventor: Dorian Lust, Columbus, WI (US)

(73) Assignee: Northstar Medical Technologies, LLC, Beloit, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,939

(22) Filed: Dec. 5, 2022

(65) Prior Publication Data

US 2023/0166988 A1 Jun. 1, 2023

Related U.S. Application Data

(63) Continuation of application No. 17/042,002, filed as application No. PCT/US2019/024758 on Mar. 29, 2019, now Pat. No. 11,518,693.

(Continued)

(51) Int. Cl.
| | |
|---|---|
| *C25B 11/00* | (2021.01) |
| *C02F 1/467* | (2023.01) |

(Continued)

(52) U.S. Cl.
CPC ............. *C02F 1/4672* (2013.01); *C02F 1/20* (2013.01); *C02F 1/46109* (2013.01); *C25B 1/13* (2013.01); *C25B 9/19* (2021.01); *C25B 9/65* (2021.01); *G01N 21/05* (2013.01); *G01N 21/25* (2013.01); *G01N 33/18* (2013.01); *C02F 2001/46142* (2013.01); *C02F 2001/46147* (2013.01); *C02F 2001/46157* (2013.01); *C02F 2201/46115* (2013.01); *C02F 2201/782* (2013.01);

(Continued)

(58) Field of Classification Search
CPC ................ C02F 1/4672; C02F 1/46109; C02F 2001/46147; C02F 2201/46115; C02F 2201/782; C02F 2209/23; C25B 9/19; C25B 9/65; C25B 1/13; C25B 11/00
See application file for complete search history.

(56) References Cited

U.S. PATENT DOCUMENTS

| | | | | |
|---|---|---|---|---|
| 2005/0252786 A1* | 11/2005 | DiMascio | ................. | C25B 1/26 204/632 |
| 2013/0032491 A1* | 2/2013 | Nitta | ..................... | C02F 1/4672 204/263 |
| 2016/0347629 A1* | 12/2016 | Ceres | .................. | C02F 1/46109 |

* cited by examiner

*Primary Examiner* — Zulmariam Mendez
(74) *Attorney, Agent, or Firm* — Husch Blackwell LLP

(57) ABSTRACT

A novel cell for generating ozonated water, the cell comprises a nafion membrane separating a diamond coated anode, and a gold surfaced cathode enclosed within a cell housing with the catalyst side of the nafion membrane facing the cathode. The cell housing has a cathode housing portion and an anode housing portion separated by the membrane, each housing portion having ridges to enhance substantially even flow of fluid over the cathode and anode. The housing portions contain O-rings in grooves to prevent leaks, and alignment features to keep the electrodes aligned. The cathode and anode have an array of holes allowing fluid to penetrate to the surface of the niobium membrane. Input ports allow fluid to flow into the housing and over the anode and cathode and then out of the housing through outlet ports. The housing may also incorporate an integrated spectral photometer including a bubble trap.

14 Claims, 6 Drawing Sheets

Related U.S. Application Data

(60) Provisional application No. 62/649,928, filed on Mar. 29, 2018.

(51) Int. Cl.
  *C02F 1/461* (2023.01)
  *C25B 1/13* (2006.01)
  *C02F 1/20* (2023.01)
  *G01N 21/05* (2006.01)
  *G01N 21/25* (2006.01)
  *G01N 33/18* (2006.01)
  *C25B 9/19* (2021.01)
  *C25B 9/65* (2021.01)
  *G01N 21/85* (2006.01)

(52) U.S. Cl.
  CPC ...... *C02F 2209/02* (2013.01); *C02F 2209/23* (2013.01); *G01N 21/85* (2013.01); *G01N 2201/062* (2013.01)

US 11,840,464 B2

SYSTEMS AND METHODS FOR OZONE WATER GENERATOR

RELATED APPLICATION

This application is a continuation of copending U.S. application Ser. No. 17/042,002 filed on Sep. 25, 2020 which is a 371 of international application PCT/US2019/024758 filed on Mar. 29, 2019 and claims priority to provisional application No. 62/649,928 filed Mar. 29, 2018 which are hereby incorporated herein by reference.

FIELD

The field relates to liquid ozone generating systems, and more particularly to a system for efficient, controlled generation of ozonated water.

BACKGROUND

Liquid oxidants such as ozonated water are widely used for cleaning and sterilization including water treatment, equipment sterilization, and food sterilization. Ozone is a strong oxidizer because its third oxygen atom can easily detach and bond with (i.e., oxidize) contaminants. Recent changes in sterile drug processing standards permit such a liquid phase ozone sterilant to be used as an alternative to heat and radiation. These cleaning and sterilization processes often require a controlled level of ozone concentration.

Known method of generating ozonated water use direct electrolysis wherein feed water is brought into direct contact with the electrolytic surface of a catalytic electrode to be electrolyzed into ozonated water. The catalytic electrode can include a cation exchange membrane, and an anode and a cathode in pressure contact with the cation exchange membrane on the respective surfaces. A feed-water supply path supplies water which comes into contact with the anode and the cation exchange membrane and the resulting ozonated water is then discharged through an ozonated water discharge path. These cleaning and sterilization processes often require a controlled level of ozone concentration.

These known devices for generating ozonated water are inefficient, inconsistent in performance and ozone concentration, often leak, and are expensive to fabricate and maintain. Thus, an improved ozonated water generator is needed.

DETAILED DESCRIPTION

Figure 1:
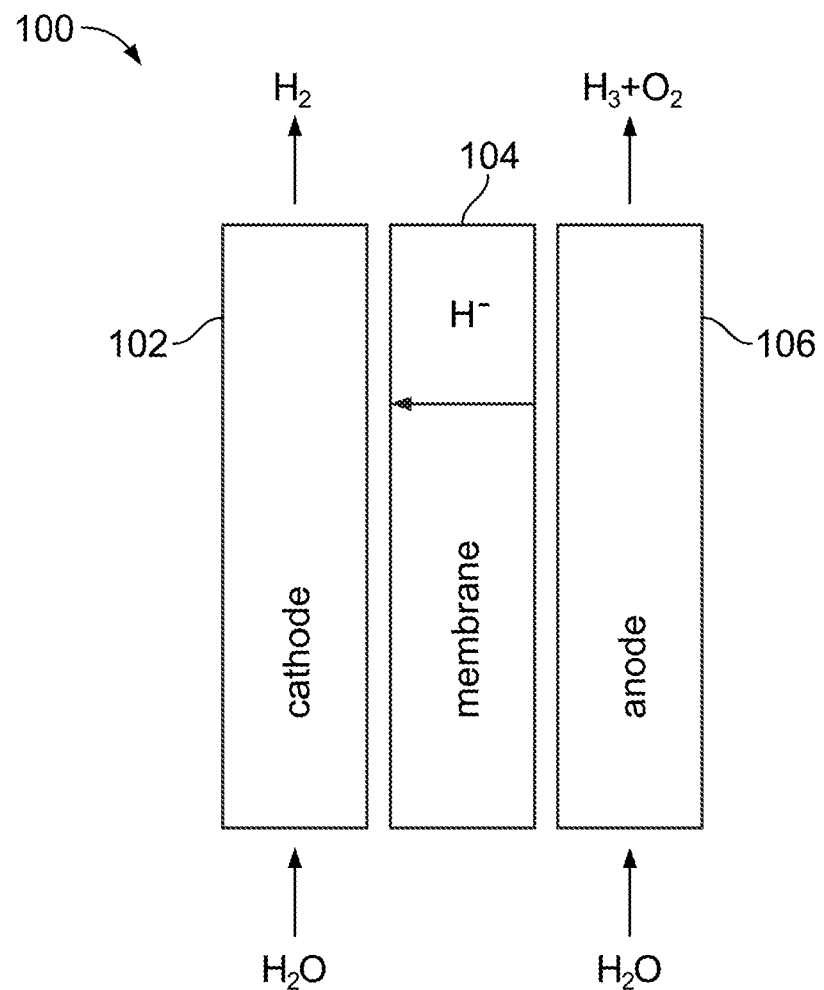
FIG. 1 is a block diagram of an example water ozonator cell, according to an example embodiment.

Example apparatus and methods for controlled ozonation of water are described herein. In the following detailed description of example embodiments of the invention, reference is made to the accompanying drawings that form a part hereof, and in which is shown by way of illustration specific example embodiments in which the invention may be practiced. These embodiments are described in sufficient detail to enable those skilled in the art to practice the inventive subject matter, and it is to be understood that other embodiments may be utilized and that logical, mechanical, electrical and other changes may be made without departing from the scope of the inventive subject matter.

Some portions of the detailed descriptions which follow are presented in terms of algorithms and symbolic representations of operations on data bits within a computer memory. These algorithmic descriptions and representations are the ways used by those skilled in the computer arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

In the Figures, the same reference number may be used to refer to an identical component that appears in multiple Figures. Signals and connections may be referred to by the same reference number or label, and the actual meaning will be clear from its use in the context of the description.

The description of the various embodiments is to be construed as examples only and does not describe every possible instance of the inventive subject matter. Numerous alternatives could be implemented, using combinations of current or future technologies, which would still fall within the scope of the claims. The following detailed description is, therefore, not to be taken in a limiting sense, and the scope of the inventive subject matter is defined only by the appended claims.

FIG. 1 is a block diagram of an example water ozonation cell 100. The cell 100 is an example in which a cathode 102 (e.g., stainless steel) is separated by a polymer membrane 104 (e.g. a nafion membrane) from an anode 106 (e.g. diamond plated niobium) as shown. In operation the cell 100 separates water into Hydrogen ($H_2$), and into oxygen in the form of $O_2$ and Ozone ($O_3$) by direct electrolysis using the polymer membrane 104. In this process, water is separated and independently introduced to the anode side of the electrolysis cell and to the cathode side of the cell. Water introduced in the anode side is electrolytically decomposed, a portion is converted to ozone, and mixes into the remaining water, thereby building the $O_3$ concentration in the water on the anode side. On the cathode side, the $H_2$ that has been separated and conveyed through the membrane is released into the water.

Advantages to producing ozone with such an electrolytic system are: 1) there is no ionic contamination because the feed-water is being disassociated using a solid hydrated ion exchange membrane; 2) the process water used for disinfection is the source of the oxygen for the generation of ozone—consequently, no outside contamination is introduced into the system being treated; and 3) the ozone is dissolved in the process water as soon as it is formed with no residual contaminants.

In the direct water electrolysis cell 100 of FIG. 1, ozone gas evolves at a voltage higher than 1.511 V, accompanied by oxygen evolution. By increasing voltage to above 2.075V, the oxidation of $O_2$ gas to form $O_3$ is also expected. Since $O_2$ evolution occurs at a lower potential than $O_3$ evolution, the production rate and electric power consumption in $O_2$ evolution are much higher than those in $O_3$ evolution. To ensure, therefore, that as much ozone as possible is produced, the anode should have an over potential above the decomposition and ozone reaction potential and the catalytic layer should inhibit the formation of diatomic oxygen and encourage the formation of ozone. This electrolysis cell design provides an efficient method of $O_3$ generation when the proper operating parameters are met. Parametric feedback may be utilized to ensure proper levels of ozone are produced in a given cell 100. A cell powered with a constant current source will have a resultant DC voltage which is in direct relation to ozone production and thus can be controlled to provide a consistent concentration of ozone. In some embodiments a desired concentration of 16 ppm of ozone can be achieved.

The cell's current density relationship to ozone generation is a factor of surface area and applied current. The current efficiency, and therefore ozone production, is stable at controlled water temperatures. In some embodiments a desired temperature between about 17° C. and 20° C. will provide a stable ozone concentration where the decay rate is matched by the generation rate. In the case of the cell 100, the constant flow rate of water, the maximum water temperature and the generation time will be factors in the stabilized ozone production concentration.

In conjunction with current and voltage, there are several other factors which affect ozone production. The factors are 1) fluid flow through the cell, 2) time of generation, 3) water pH and purification, 4) total water volume, and 5) water temperature. The cell 100 permits monitoring and regulating the above-mentioned five factors at a steady-state so as to significantly diminish the variable effects on ozone production. The fluid flow may be monitored and regulated to ensure it maintains a constant flow rate. The time of cell operation to generate ozone may be set to a defined duration. The water input is preferably USP sterile water which controls the pH and eliminates any contaminants. The input water volume may be monitored and controlled to ensure repeatable levels are sustained during the ozone generation cycle. The water temperature may be monitored and regulated to ensure it does not exceed a predetermined threshold.

Figure 2A:
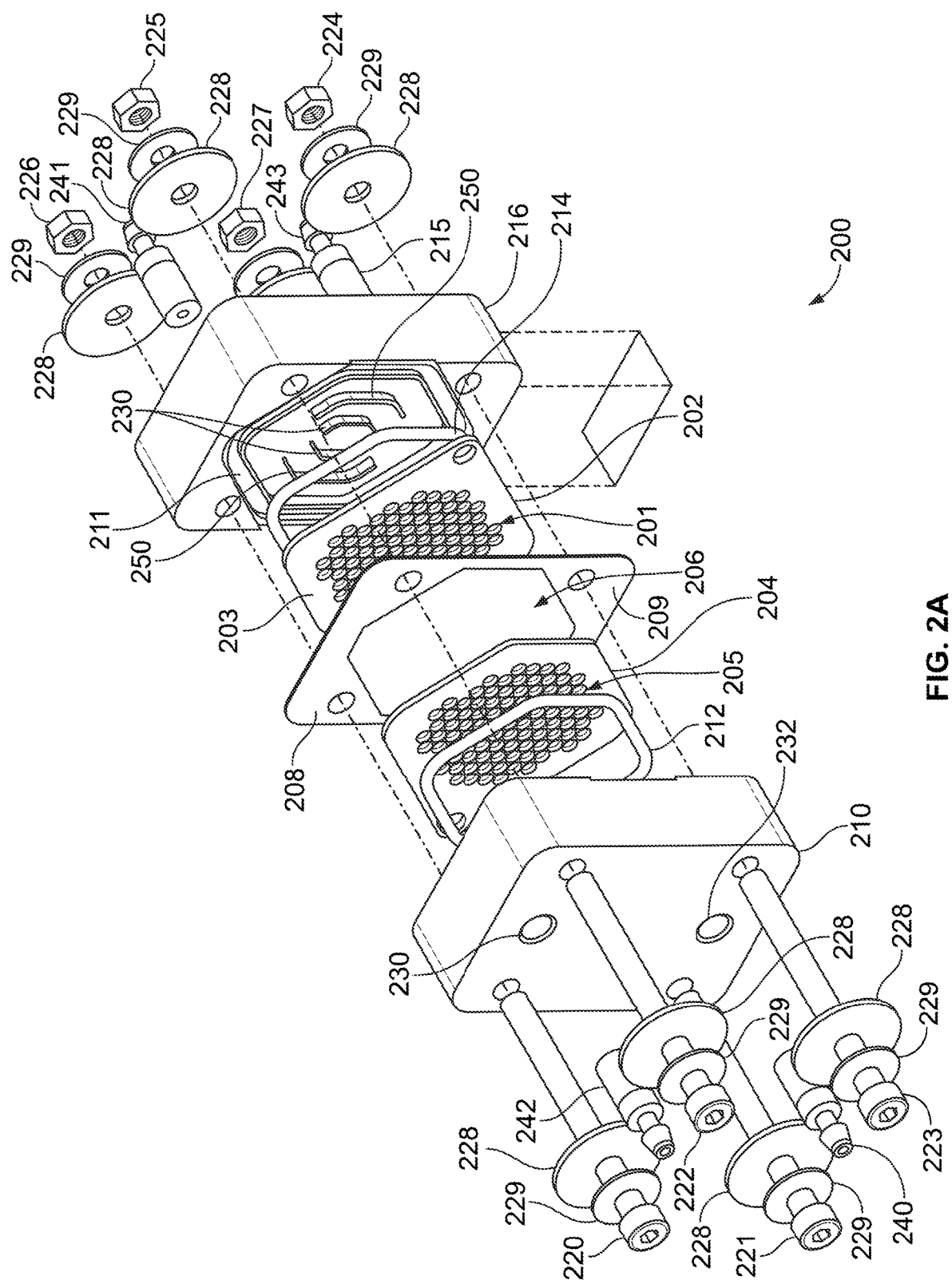
FIG. 2A is a an exploded view of an example ozonator cell device, according to an example embodiment.

FIG. 2A illustrates an exploded view of an embodiment of a novel ozonation cell 200 which is a specific example embodiment of the cell 100 of FIG. 1. The cell 200 comprises an anode 202 having a diamond coating on the side 203 facing a cathode 204 separated by a membrane 206. In the illustrated embodiment of FIG. 2A, both the anode 202 and the cathode 204 have an array of small holes 201, 205 that extend through the electrodes 202, 204. In one embodiment the anode 202 may be composed, for example, of niobium plated with a thin layer of doped diamond and the cathode 204 may be composed, for example, of stainless steel plated with gold.

The anode 202 may be any suitable conductor and is preferably niobium (or some other suitable material) coated with a layer of doped diamond. In one embodiment the niobium is about 99% pure and the diamond layer is about 2 microns thick. An array of holes 201 in the anode 202 allows water to contact the membrane 206 on the anode side while porosity of the membrane 206 allows the water to spread out between the holes of the array to wet the surface of the membrane 206 between the holes. The array of holes 201 of the anode 202 in one embodiment covers at least 75% of the surface area of the anode exposed to water (i.e., the area within the O-ring 214). In one embodiment the holes 201 are about 70 thousandths of an inch in diameter and should be large enough to allow water to adequately contact the membrane 206.

In some embodiments, the niobium anode surface is first anodized to create pores to promote surface adhesion, and then the doped diamond plating is applied. In other embodiments, the niobium surface may be bead blasted first and then etched to create an optimal surface texture to increase surface adhesion of the diamond plating In other approach, sputtering niobium onto the base material using a mask may be used to create surface texture to improve adhesion. In yet another embodiment the anode may be made of a thin mesh of niobium to maximize surface area, the mesh anode surface may then be prepared by any suitable method such as those described above which is then coated with a doped diamond layer. The diamond layer of the anode is preferably doped (i.e., doped with boron) to a concentration sufficient to make the diamond layer conductive. The diamond layer in some embodiments may be approximately two microns thick.

The cathode 204 is composed of a suitable conductor (e.g., stainless steel, gold, silver, etc.) which does not interact excessively with the fluid, preferably a gold surfaced electrode. In some embodiments the cathode 204 may be stainless steel plated on both sides with gold to create a gold surface to eliminate interaction of the water with iron. The cathode 204 also includes the array of holes 205 as shown. The array 205 in some embodiments covers at least 75% of the surface area of the cathode which is exposed to water (i.e., the area enclosed within the O-ring 212). The holes allow water to contact the membrane 206 on the cathode side while porosity of the membrane 206 allows the water to spread out between the holes to wet the full surface covered by the array of holes 205 between the holes. In one embodiment the holes 205 are approximately 70 thousandths of one inch in diameter.

In the illustrated embodiment, the cathode 204 and anode 202 are separated by a polymer membrane 206, for example a nafion membrane. The membrane may contain a conductive diffuser oriented with the diffuser side 208 facing the cathode, as shown. The membrane may also contain a platinum catalyst on the side facing the cathode. In the illustrated embodiment an O-ring 212 (e.g. silicone) is located between the cathode 204 and a body element 210 to form a seal therewith, and a second O-ring 214 is located between the anode 202 and a second cell body element 216 to form a seal to minimize leakage of water from around the edge of the electrodes 204 and 206. In one embodiment, the membrane 206 is about 10 thousandths of an inch thick. The membrane 206 may absorb water so a double sided adhesive border 209 may be adhered to the membrane 206 to enhance the seal around the edges. A groove 211 may be formed in each body element 210, 216 to receive the O-rings.

In one embodiment, the body elements 210, 216 may be composed of ozone resistant high density polyethylene or CPVC. Four bolts 220-223 together with nuts 224-227 and washers 228, 229 hold the body elements 210, 216 together to form an enclosure while holding the cathode 204, anode 202 and membrane 206 in place and properly aligned within the enclosure. Water inlet/outlet ports 230, 232 allow entry and exit of water to and from the cell 200. Water inlet/outlet adaptors 240, 242 are mounted to the ports 230, 232 to allow connection of water tubing. Ridges 250 may be formed in the inner surface of each body element 210, 216 to enhance the water flow pattern so that the water passes relatively evenly across the full face of the anode 203 and cathode 204 as it passes through the cell.

Figures 2B, 2C:
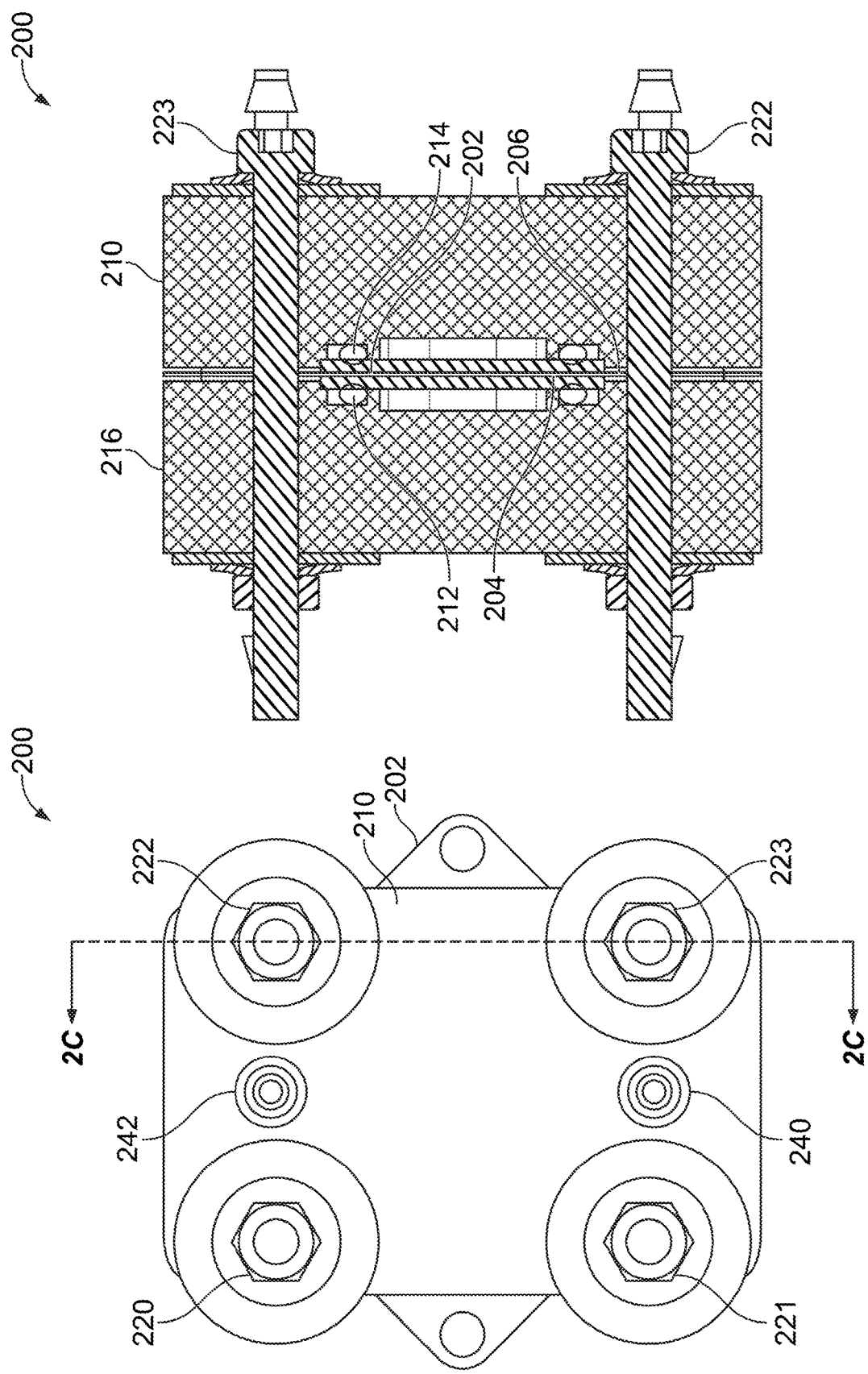
FIG. 2B is a side view of the example ozonator cell of FIG. 2A.
FIG. 2C is a cross-sectional view of the example of FIG. 2A.

FIG. 2B illustrates an end view of the ozonation cell 200 with the bolts 220-223 and inlet/outlet adaptors 240, 242. FIG. 2C illustrate a cross-sectional view of the cell 200 along the line AA of FIG. 2B showing the body elements 210, 216 held together by the bolts 222, 223. Shown between the two body element 210, 216 are the O-ring 212, 214, the membrane 206, the cathode 204 and the anode 202. In some embodiments the bolts 220-223 are torqued to a desired level to control pressure on the electrodes. In one embodiment the bolts are torqued to approximately 6 ft-lbs to provide sufficient tightness while allowing water to flow on both sides contacting the nafion membrane 206 and to allow current to pass through the cell.

During operation of the cell 200, dc voltage is applied across the cell with the negative applied to the cathode and positive side to the anode. Water is pumped through the cell 200 entering the cathode side through the inlet port 232 to flow across the face of the cathode 204 and out of the cell 200 through the outlet port 230. The water is supplied via tubing connected to the outlet adapter 240, and flows out via tubing connected to the outlet adaptor 242. Similarly water enters the anode side of the cell 200 through the inlet port 215, from tubing connected to the inlet adapter 243, flows across the face of the anode 202 and out of the cell 200 via the outlet port and outlet adaptor 241. The water flowing on each side contacts the membrane 206 through the holes 201, 205. The water flow rate, water temperature, cell voltage and current are monitored and controlled to control the ozone concentration out of the cell 200.

In an alternative embodiment, the ozonation cell may include an integral spectral photometer to allow monitoring and control of ozone concentration. The spectral photometer portion projects UV light through the water flowing through a transparent chamber to measure ozone concentration. The integral spectral photometer also incorporates a bubble trap.

Figure 3:
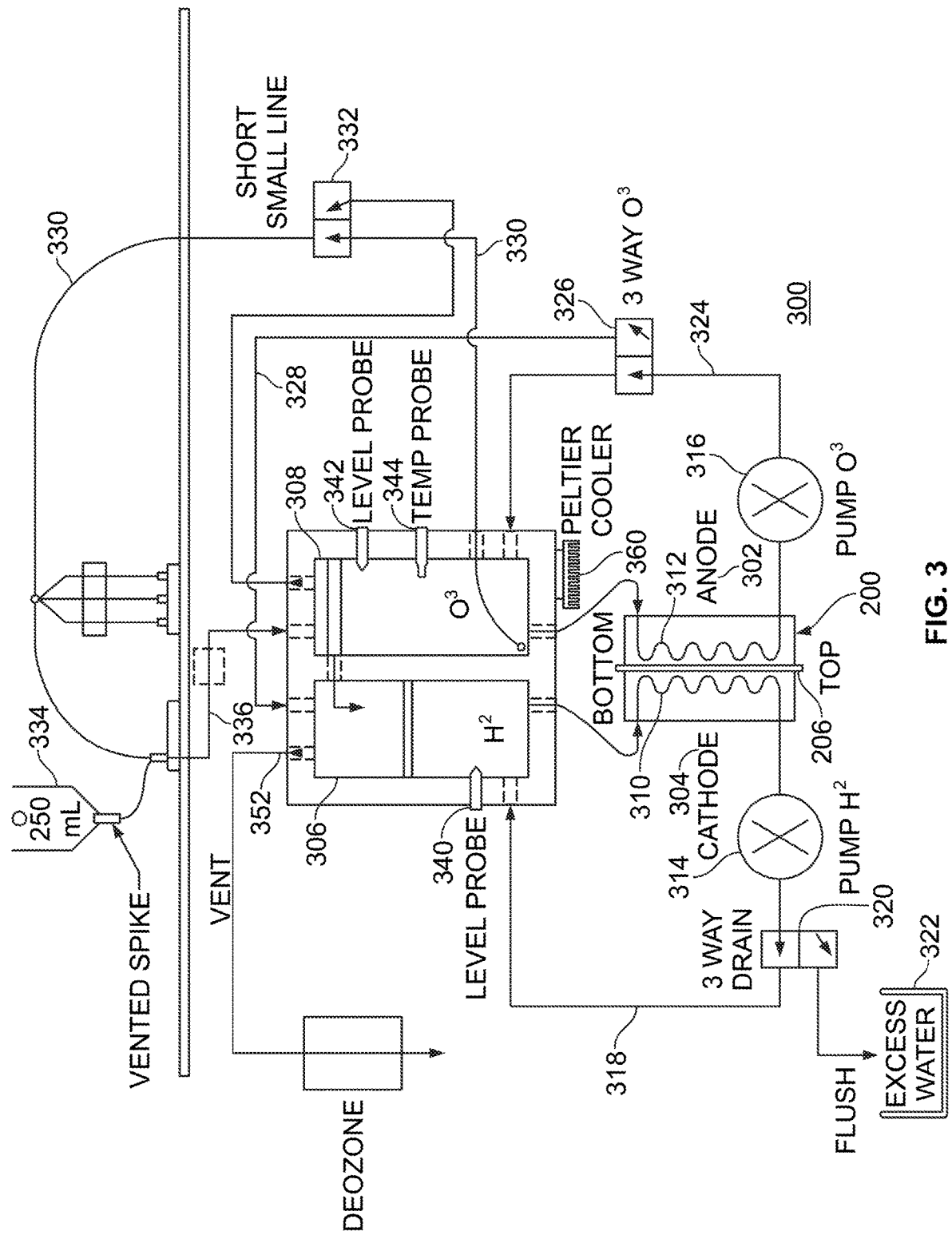
FIG. 3 is a functional diagram of an example system utilizing an ozonator cell.

FIG. 3 illustrates a functional diagram of an embodiment of an example water ozonation system 300, according to an example embodiment. The system 300 as shown includes an ozonation cell 200 having a cathode side 304, an anode side 302, and the membrane 206. The cell 200 is coupled to a pair of water reservoirs 306, 308 as shown. The reservoirs 306, 308 may be sized as needed, for example, in one embodiment, holding 50 ml and 200 ml, respectively. Fluid flows through the cell 200 via a cathode path 310 and an anode path 312. The fluid is driven through the cathode path 310 by a pump 314 which returns fluid with hydrogen to the hydrogen side reservoir 306 via a tubing path 318 through a three way valve 320 which can direct fluid into an excess fluid receptacle 322, as shown, to flush excess fluid. The fluid is pumped through the anode path 312 by a pump 316 via a tubing path 324 to the ozone reservoir 308 through a three way valve 326 which can also direct fluid to the reservoir 306 via a path 328, as shown. Also, in the illustrated embodiment, fluid can also be channeled from the bottom of the reservoir 308 via path 330 through a three way valve 332 to the top of the reservoir 308. A source of fluid is provided from a reservoir 334 to the reservoir 308 via a path 336. The reservoir 334 may be sized to hold a suitable amount for fluid, for example, in one embodiment, 250 ml of water. Levels in the reservoirs 306, 308 are monitored by level sensors 340, 342 and fluid temperature in the ozone reservoir 308 is monitored using temperature sensor 344. A cooler 350 (e.g. a Peltier cooler) permits control of fluid temperature in the reservoirs 308. A vent 352 provides a path for venting of excess gas from the reservoirs 306, 308.

Water from the ozone reservoir 308 is circulated to maintain a desired ozone level in the water while water is drawn out to be used for sterilization. The ozone concentration is controlled by controlling the voltage across the cell 200 and the current through the cell 200. A control board 400 (see FIG. 4) can monitor the cell 200 current and voltage and fluid temperatures to control ozone generation.

Figure 4:
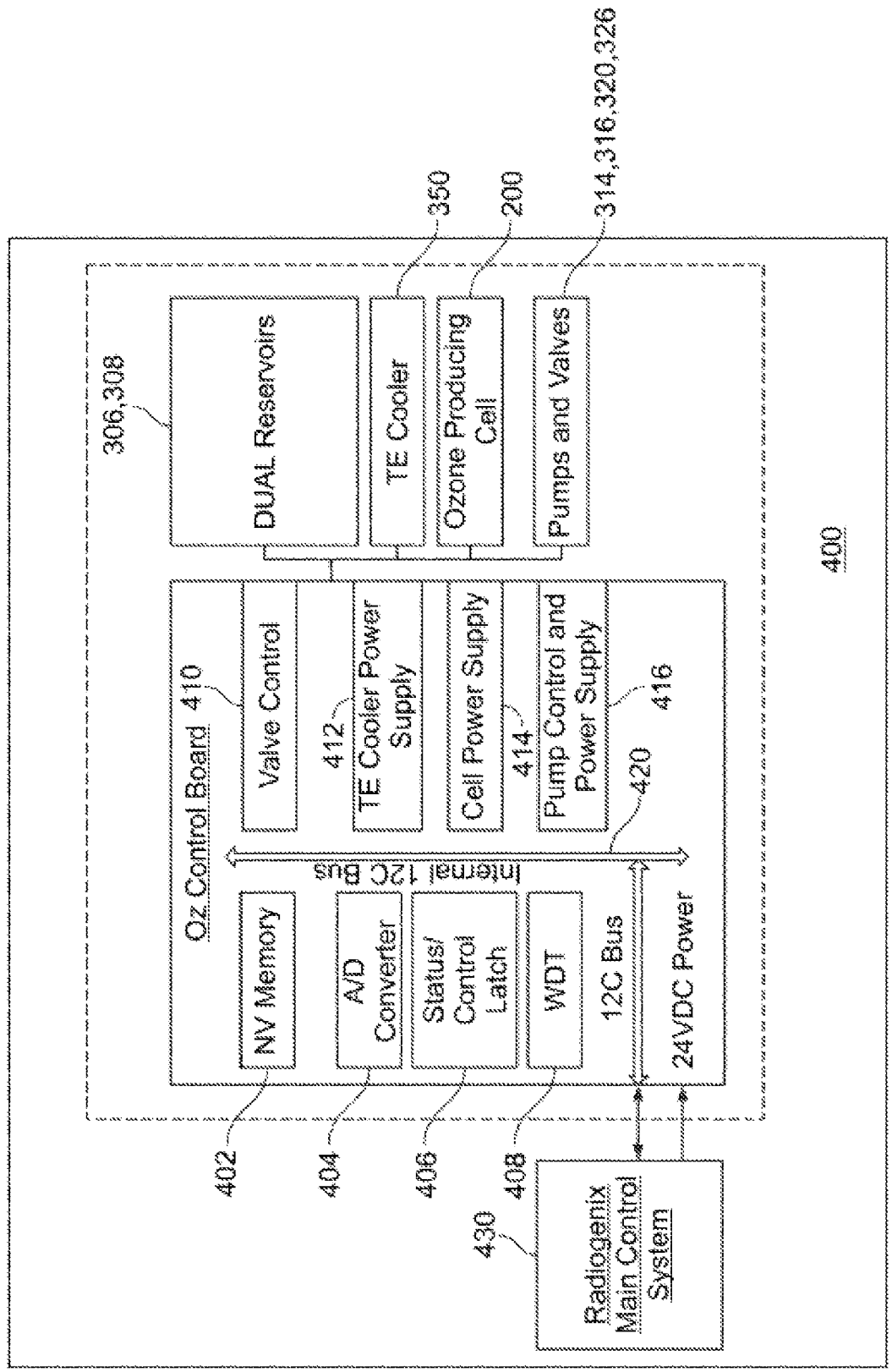
FIG. 4 is a functional block diagram of an example embodiment of control circuitry for the system of FIG. 3.

FIG. 4 illustrates a functional block diagram of an example of control circuitry 400 to control the exemplary embodiment of FIG. 3. The control circuitry 400 includes a memory 402, an A/D converter 404, control latch 406, WDT 408, valve control 410, cooler power supply 412, cell power supply 414 and pump control and power supply 416 communicating via a bus 420. The circuitry 400 is coupled, as illustrated to the reservoirs 306, 308 (i.e. to the sensors 340, 342, 344), to the cooler 350, and the cell 200. The control circuitry 400 is controlled by a controller 430 coupled via the bus 420.

Figure 5:
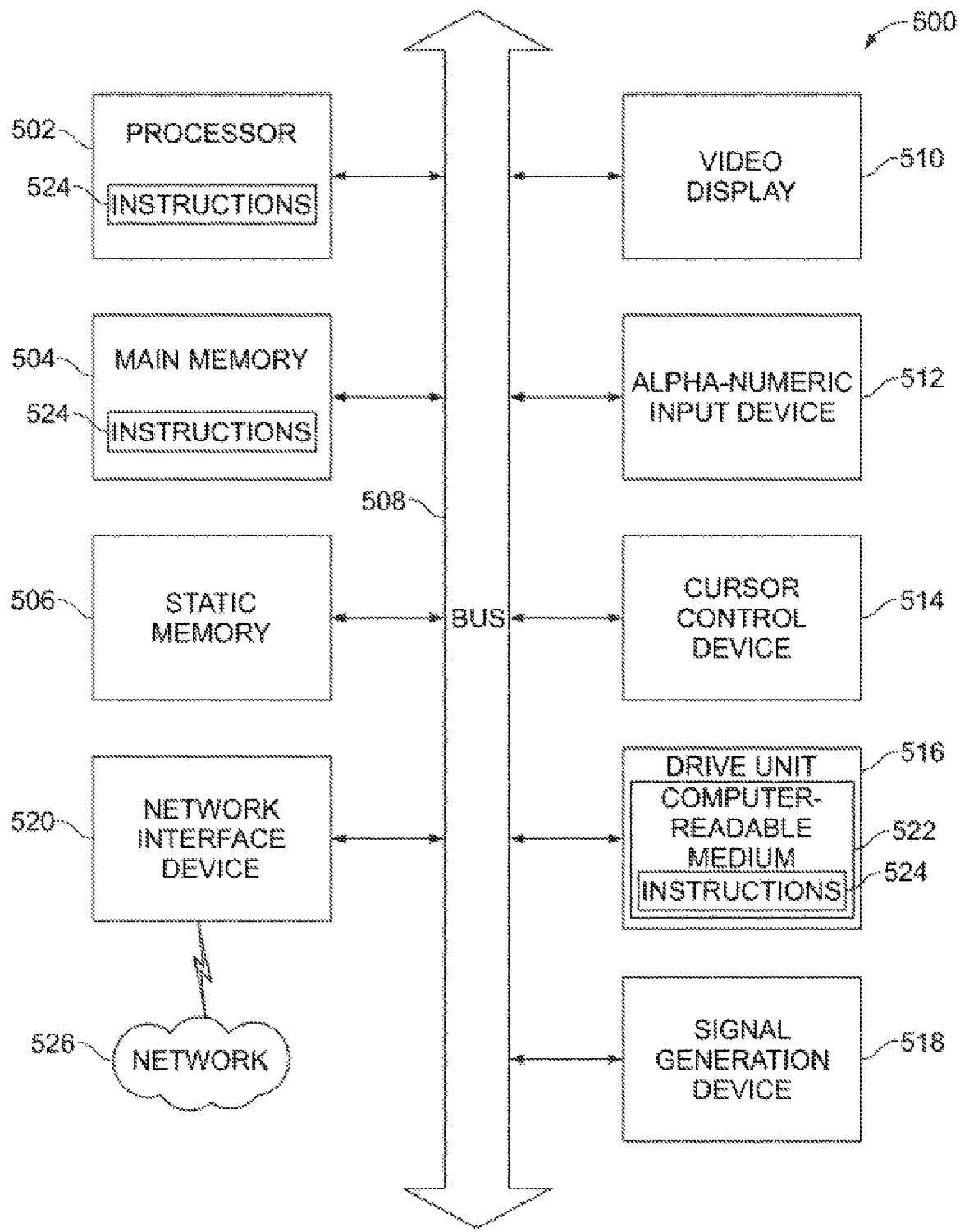
FIG. 5 is a block diagram of an example computer system within which a set of instructions for causing the machine to perform any one or more of the methodologies discussed herein may be executed or stored.

FIG. 5 shows a block diagram of an example embodiment of a machine in the form of a computer system 500 within which a set of instructions may be executed causing the system to perform any one or more of the methods, processes, operations, or methodologies discussed herein. The controller 430, for example, may include the functionality of the one or more computer systems 500.

The description of FIG. 5 is intended to provide a brief, general description of suitable computer hardware and a suitable computing environment in conjunction with which aspects of the invention may be implemented. In some embodiments, aspects of the inventive subject matter is described in the general context of computer-executable instructions being executed by a computer.

Those skilled in the art will appreciate that the aspects of the disclosure may be practiced with other computer system configurations, including hand-held devices, multiprocessor systems, microprocessor-based or programmable consumer electronics, smart phones, network PCs, minicomputers, mainframe computers, and the like. Aspects of the disclosure may also be practiced in distributed computer environments where tasks are performed by I/O remote processing devices that are linked through a communications network. In a distributed computing environment, program modules may be located in both local and remote memory storage devices.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, imbedded controller, a cellular telephone, a network router, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 500 may include a processor 502 (e.g., a central processing unit (CPU), a graphics processing unit (GPU) or both), a main memory 504 and a static memory 506, which communicate with each other via a bus 508. The computer system 500 further includes a video display unit 510 (e.g., a liquid crystal display (LCD) plasma, or a cathode ray tube (CRT)). The computer system 500 also includes an alphanumeric input device 512 (e.g., a keyboard), a cursor control device 514 (e.g., a mouse), a drive unit 516, a signal generation device 518 (e.g., a speaker) and a network interface device 520.

The disk drive unit 516 includes a computer-readable medium 522 on which is stored one or more sets of instructions (e.g., software 524) embodying any one or more of the methodologies or functions described herein. The software 524 may also reside, completely or at least partially, within the main memory 504 and/or within the processor 502 during execution thereof by the computer system 500, the main memory 504 and the processor 502 also constituting computer-readable media. The software 524 may further be transmitted or received over a network 526 via the network interface device 520.

While the computer-readable medium 522 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, transitory and non-transitory media. Examples of non-transitory media include but are not limited to solid-state memories, optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

Such embodiments of the inventive subject matter may be referred to herein, individually or collectively, by the term "invention" merely for convenience and without intending to voluntarily limit the scope of this application to any single invention or inventive concept if more than one is, in fact, disclosed.

As is evident from the foregoing description, certain aspects of the inventive subject matter are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the inventive subject matter. Therefore, it is manifestly intended that this inventive subject matter be limited only by the following claims and equivalents thereof.

The methods described herein do not have to be executed in the order described, or in any particular order. Moreover, various activities described with respect to the methods identified herein can be executed in serial or parallel fashion.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A cell system for ozonation of water comprising:
   a cathode having a gold surface and an anode, separated by a polymer membrane, the anode and cathode each have an array of holes to allow water to flow through to the membrane;
   a housing enclosing the cell and having a cathode housing portion and an anode housing portion separated by the membrane, the cathode housing portion configured to allow water to flow across the cathode and the anode housing portion configured to allow water to flow across the anode, each housing portion having ridges arranged to direct water flow evenly over the cathode and the anode; and
   input and output housing to allow water to flow separately through both portions of the housing.

2. The cell of claim 1 wherein the membrane is a nafion membrane.

3. The cell of claim 2 further comprising a first O-ring between the cathode housing portion and the cathode, and a second O-ring between the anode housing portion and the anode.

4. The cell of claim 1 wherein the anode is made of niobium.

5. The cell of claim 4 wherein the anode is plated on at least one side with a diamond layer.

6. The cell of claim 1 wherein the input ports are configured to be coupled to a pump to pump water through the housing and over the cathode and anode.

7. The cell of claim 3 wherein the cathode housing portion further comprises a groove for receiving the first O-ring and the anode housing portion further comprising a groove for receiving the second O-ring.

8. The cell of claim 5 wherein the diamond layer is doped with boron.

9. The cell of claim 1 wherein the cathode is made of stainless steel plated with gold.

10. The cell of claim 1 wherein the array of holes covers at least 75 percent of each electrode's surface area exposed to the fluid.

11. The cell of claim 1 wherein the anode is composed of a niobium electrode having a textured surface which is coated with a diamond layer.

12. The cell of claim 1 wherein the anode is a thin niobium mesh coated with a layer of doped diamond.

13. The cell of claim 1 wherein the housing maintains alignment between the anode and the cathode.

14. The cell of claim 1 further comprising an integrated spectral photometer including a bubble trap to measure ozone concentration.

\* \* \* \* \*